(12) United States Patent
Weickmann

(10) Patent No.: US 8,367,119 B2
(45) Date of Patent: Feb. 5, 2013

(54) PHARMACEUTICAL COMPOSITION, USE OF THE PHARMACEUTICAL COMPOSITION FOR TREATING A BRAIN TUMOR, PRODUCTION PROCESS THEREOF AND A KIT OF PARTS COMPRISING THE PHARMACEUTICAL COMPOSITION

(75) Inventor: Dirk Weickmann, Ansbach (DE)

(73) Assignee: ABiTec Angewandte Bio-Technologie GbR, Munich (DE)

( * ) Notice: Subject to any disclaimer, the term of this patent is extended or adjusted under 35 U.S.C. 154(b) by 370 days.

(21) Appl. No.: 12/520,258

(22) PCT Filed: Dec. 20, 2007

(86) PCT No.: PCT/EP2007/064355
§ 371 (c)(1),
(2), (4) Date: May 14, 2010

(87) PCT Pub. No.: WO2008/074872
PCT Pub. Date: Jun. 26, 2008

(65) Prior Publication Data
US 2011/0038846 A1 Feb. 17, 2011

(30) Foreign Application Priority Data
Dec. 20, 2006 (DE) .......................... 10 2006 060 344

(51) Int. Cl.
*A61K 35/48* (2006.01)
*A61K 35/64* (2006.01)

(52) U.S. Cl. ......... 424/541; 424/542; 530/300; 530/350

(58) Field of Classification Search .................. 424/541, 424/542; 530/300, 350
See application file for complete search history.

(56) References Cited

U.S. PATENT DOCUMENTS
6,998,389 B2 2/2006 Weickmann

FOREIGN PATENT DOCUMENTS
WO WO2005/004887 1/2005
WO WO 2006134166 A2 * 12/2006

OTHER PUBLICATIONS

Khvotchev et al. EMBO Journal (2000) 19(13): 3250-3262).*
Fry et al. Rapid Comm. Mass Spec. (2003) 17: 2047-2062.*
Binford et al. Comparative Biochem. Physiol. part B (2003) 135: 25-33.*
Yang et al. Dongwu Xuebao (2007) 53(4): 682-688 (abstract; downloaded from STN on Mar. 10, 2012).*
Machine translation for CN 1682981 (published Oct. 19, 2005) downloaded from the SIPO website Oct. 14, 2012.*
Machine translation for DE 102005027665 (publsihed Dec. 21, 2006) downloaded from the EPO Oct. 12, 2012.*
STN abstract for CN 1682981, downloaded from CAPLUS Oct. 14, 2012.*
Bettini, S., On the mode of action of *Latrodectus* spp. venom. *Annali Dell Instituto Superiore Di Sanita.* vol. 7, No. 1 pp. 1-7 (1971).
Notification of Transmittal of the International Search Report corresponding to International Patent Application No. PCT/EP2007/064355 dated Mar. 10, 2008.

* cited by examiner

*Primary Examiner* — Susan Hanley
(74) *Attorney, Agent, or Firm* — Jenkins, Wilson, Taylor & Hunt, P.A.

(57) ABSTRACT

The invention relates to the pharmaceutical composition for the treatment of a brain tumor, which contains in an effective amount from pharmaceutical point of view Peptidtoxin from spiders, *Sicarius* species and/or the saliva of the vipers from the *Elaphe* species; and the total poison or part of the spiders poison from the *Latrodectus* species, as well as the use of the pharmaceutical composition for the treatment of the brain tumor, a process for producing the pharmaceutical composition as well as a kit of parts containing the pharmaceutical composition.

17 Claims, No Drawings

PHARMACEUTICAL COMPOSITION, USE OF THE PHARMACEUTICAL COMPOSITION FOR TREATING A BRAIN TUMOR, PRODUCTION PROCESS THEREOF AND A KIT OF PARTS COMPRISING THE PHARMACEUTICAL COMPOSITION

The invention relates to a pharmaceutical composition, the use of the pharmaceutical composition to treat a brain tumor, manufacturing processes, and a kit of parts containing the pharmaceutical composition.

Annually around 7000 cases of serious brain tumor occur in Germany, which include astrocytoma with malignancy grades II and III as well as grade IV glioblastoma and multiforme glioblastoma. Brain tumors are often diagnosed as a secondary result. They often occur in patients with bleeding in the cervical and skull regions, which can be associated with loss of consciousness and/or severe pain. Thus, the admission of patients into a hospital is typically necessary.

Brain tumor treatment is presently very cumbersome. Particularly due to the emergence of glioblastoma, often the prognosis is not positive for patients. The symptoms can be alleviated by removing the tumor with surgery, but the duration of the patient's life can generally be extended for only a few months. Long term recovery is very rare.

Current therapies against tumors, the most dangerous and most feared disease of our era, attempt to combat tumors in a very radical way that is frequently not very patient-friendly. In this regard, we present a few simple keywords: surgery, radiation, and chemotherapy. This means that once that the tumor, if reasonably accessible, is in principle removed with the scalpel, destroyed by a wide range of radiation, or by so-called chemotherapy, which through aggressive cytostatic actions can also affect healthy cells. Both with normal treatment and with surgery as well as with radiation, spatial delimitation of the treatment area is not possible. These treatments inevitably also destroy healthy cells of the body. The adverse side effects of chemotherapy are well known, as are the disadvantages of radiotherapy.

In particular, the surgical removal brain tumors, however, has more side effects. Often a second operation on the patient is required. During the first operation and the removal of the brain tumor a large stigmatic surface is produced. In addition to healthy glial cells, diseased glial cells can also be deposited, i.e., malignant glial cells. These are often cells derived from the tumor and generate metastases. Thus a diffuse recurrence is inevitable. This cannot be treated by conventional methods. Therefore, they are often fatal to the patients.

After the surgery, usually radiotherapy and/or chemotherapy follows. In chemotherapy, typically Cisplatin is used in various combinations. Since the beginning of 2002 a medicine for oral administration with the name Temozolomid (Essex Company) is used. Temozolomid has the trade name TEMODAL®. And GLEEVEC® is another cytostatic that can be used. In addition to the known side effects such as vomiting, malaise, and depression caused by cancer chemotherapy and nervous disorders, a problem with the above-mentioned treatments is that in order to treat a brain tumor they must cross the blood-brain barrier. Typically, active compounds cross the blood-brain barrier with an efficiency of only about 0.4 to 5%. The composition and functioning of the blood-brain barrier are still only preliminarily understood. This barrier is intended to protect the brain from harmful substances, but on the other hand, it allows a limited input power.

Our body is composed of individual organic systems and organs, which require for their operation different but constant conditions, such as nutrients, hormones, and electrolytes. All the organs are linked by the blood circulation. Because all the components needed for the nourishment are found in the blood, but also for the detoxification of the body, the filtering systems are careful to allow only the passage of substances necessary to certain organic systems. In this connection are designated inter alia the blood barrier of the tissues, also called the blood barrier of the parenchyma, the blood barrier of the liver, the blood barrier of the cerebrospinal fluid (CSF), the blood-brain barrier, the CSF barrier of the brain, the blood barrier of the nerves, the blood barrier of the retina, and the barrier of the placenta.

By these filtering mechanisms, through the so-called barrier effect, the passage of certain substances in the blood stream is restricted to prevent the passage to the organs system in cases in which the components are not necessary or are required in a small amount for these organs systems.

These "barriers" are not independent organs, but are composed of a series of cells and spaces between the cells, and allow the passage of the blood, of nutrient substances, and of certain chemicals, or retain them as endothelial macromolecules. They may have the effect of a lipid membrane in the wall of the vessels for the passage of substances which do not dissolve in lipids, or may have a selective effect on the active process of transportation in the capillaries. The brain and the nervous tissue are protected by two systems of filtration, the blood-CSF barrier and the blood-brain barrier.

The existence and the functioning of the so-called blood-brain barrier has been known for more than 100 years and has been demonstrated through experiments by Paul Ehrlich in 1885. In the central nervous system the spaces between the neurons are almost totally filled by glial cells and their processes. The entire metabolism of the nerve cells is carried out by these glial and endothelial cells. They contribute to the formation of the nerves cells and of the nerves fibers as well as to their alimentation and isolation. A form of the glial cells are the astrocytes. They have many extensions with which they are held to the wall of the capillaries and constitute an endothelial surface without descents surrounding all sides. These endothelial cells are linked by connecting elements, "tight junctions", and equipped with a selective filter for passage of substances, allowing the passage of particles with a diameter of less than 20 nm. In this way, general metabolism is conducted through this endothelial netting, which allows, like a biological filter, the passage of the substances in the blood according to need, but retains substances that are dangerous for the functioning of the brain at a distance from the nervous system.

The endothelial knitting and the endothelial cells that surround the capillaries like a basal membrane are referred to as the blood-brain barrier. Acidic substances, carbon dioxide, D-glucose, D-hexose, certain L-amino acids, and substances necessary for the nutrition of the brain are allowed to pass without restriction. In the same way, decomposition products are returned to the blood. The final processes of the astrocytes constitute a barrier for certain hormones, substances which do not dissolve in lipids, substances which dissolve in water, and chemicals, such as proteins, and ensure in this way the maintenance of a constant environment for the nervous system neurons.

The astrocytes' cell structure is so ordered that it constitutes an obstacle to high molecular weight substances and organisms. However, under normal conditions it is not fully sealed, so certain particles can always pass through this barrier. In the case of infection, trauma, inflammation, poisoning, hypoxia, fever, and in the range of tumors, the close links of the tight junctions between the endothelial cells are dilated by the inflammation of the astrocytes and become significantly more permeable to other substances. The modification of the distance is the consequence of the swelling and of the deflation of the endothelial cells. Also the basal membrane of the capillaries is not a closed layer. Depending on the density of the fiber mesh, pores are constituted in the membrane which participate actively in the exchange of substances.

Long before the possibility of treatment with antibiotics, the capacity of crossing the blood-brain barrier has been increased by artificially producing fever, similar to an infection process, for the therapy of syphilis of the central nervous system, and for shock therapy in psychiatry, and the possibility of administration of medicines directly to the brain has arisen. After the cessation of conditions that influence the blood-brain barrier, the temporary permeability of the blood-brain barrier is reformed.

For chemotherapy of the patients with brain metastasis of solid tumors, treatment with Termozolomid (TERMODAL®), a lipophilic alkylating agent, has been clinically researched. It weakens the blood-brain barrier and increases the sensitivity of the tumor to radiation in case of simultaneous radiotherapy.

In contrast to this, the possibility of conducting brain therapy in a more subtle way, based on natural products, has also been researched.

In this respect, among others, many substances extracted from poisonous organisms with increased effects in therapeutic doses can be used.

The use of these biological poisons began early in human history. For safe use of these poisons, however, it was initially necessary for basic knowledge regarding the treatments and their effects was required. Further research relating to deciphering the chemical composition of these biological poisons thereafter led by targeted investigations of certain active substances to a proper use of the substances, which has led to the observed effects.

A powerful boost in separation technology, which is a path to ascertain the active substances to fight against diseases, was made by the discovery of the chromatographic process in the middle of the 20th Century. Starting from the division between a mobile phase and a stationary liquid, the absorption, the sieve effect of the molecules, the change of ions, affinity (especially of proteins) to defined chemical relations (e.g., enzymes substrate) and the mobility of the molecules in the electric field, a variety of new separation techniques have been developed.

Just recently, many active pharmaceutical substances have been developed from biological toxins.

From PCT/EP00/19202 is known an active pharmaceutical substance, for which it has been found that certain components of the venom of spiders can be used. A peptide toxin extracted from the poison of this species of spiders, a substance extracted from the poison with antagonistic effect, and/or a combination of these components can be used medically. The use of the peptide toxin for example from species of the genus *Sicarius* is recommended for treating breast carcinoma, lung carcinoma, adenocarcinoma, liver carcinoma, as well as melanoma. The possibility of treating brain tumors, such as astrocytoma and the glioblastoma, is not mentioned. Consequently, the problem of passing through the blood-brain barrier is not discussed.

The active substances described in PCT/EP00/19202 may be used to treat disease with tumors, as well as in parallel or as a support in treatments of tumors and tissue debris from tumors. In therapy, genetically modified cells from the body (tumor cells) can be destroyed, whereas the active substance recognizes the modified structure of the surface of these cells and it eliminates them without complications. The complete venom of these species of spiders, a so-called cocktail of different substances, cannot be used from a pharmaceutical point of view because of it can be fatal, even in small doses.

However, this known active substance does not have an effect in vivo on brain tumor, and especially on a special type of brain tumor, such as a oligodendroglioma or oligodendrocytoma. It is necessary for successful therapy for this active substance to pass the blood-brain barrier in a large amounts.

Another combination of poisonous substances is disclosed in PCT/EP2006/063281. The published combination of the various poisonous substances partially neutralized each other, however, and the destructive effect on the tumor cells was unsatisfactory.

It was surprisingly found that the peptide toxin from *Loxosceles* unbinds the peptide toxin of the *Latrodectus*, so that the peptide toxin from *Loxosceles* passes in an insignificant quantity through the blood-brain barrier. After mixing of the peptide toxin of the *Latrodectus* and of the *Loxosceles*, no distinct bands were observed: merely a smear caused by the fragments of the peptide digest of *Latrodectus* peptide toxins. The spiders of the genus *Loxoceles* belong, as well as those of the genus *Sicarius*, to the family Sicariidae. Based on the tight relationship between the two spider species, any effect of the mixture of the peptide toxin of the *Sicarius* species with the one of the *Latrodectus* species cannot be expected.

Therefore, an object of the present invention is the production of a composition that, by passing the blood-brain barrier as effectively as possible, results in the destruction of cancer cells in the body without giving rise to complications, in particular in the area of the brain, especially with respect to the rare brain tumor, oligodendroglioma.

Another object of the present invention is to provide a method for manufacturing a pharmaceutical composition for treating a brain tumor.

Another object of the present invention is to provide a combination of active substances that facilitate effective treatment of brain tumors.

These objects are achieved by the features of the independent claims. Preferred improvements and embodiments of the invention are found in the dependent claims.

A first aspect of the present invention relates to a pharmaceutical composition for treating the brain tumor that contains in a pharmaceutically effective amount:
  a.) peptide toxin of spiders of the genus *Sicarius* and/or the saliva of the vipers of the genus *Elaphe*; and
  b.) total poison or part of the poison of spiders of the genus *Latrodectus*.

The peptide toxin of the spiders from the genus *Sicarius* and/or the saliva of the vipers of the genus *Elaphe* are able to destroy the cells of a tumor. By combination with the poison of the spiders of the genus *Latrodectus*, the poison that destroys the tumor is transported through the blood-brain barrier into the brain, and there it that can fight against the tumor. The venom of the spiders of the genus *Latrodectus* has an effect on substances that pass through the blood-brain barrier. For the first time this combination makes it possible to destroy the cells of tumors in the brain. Unexpectedly, the peptide toxins from *Latrodectus* were not degraded by the peptide toxins from *Sicarius*, so the peptide toxins from *Latrodectus* acted as transfer substances for the other toxins that are tumor cell destroyers and have passed the blood-brain barrier, and then by contact with the peptide toxins from *Sicarius* and/or *Elaphe* could destroy the tumors in the area of the brain, for example oligodendrocytes.

Subsequently, it was surprisingly found that the peptide toxins from *Elaphe* are also able, in contact with the peptide toxins from *Latrodectus*, to pass the blood-brain barrier, and to kill the astrocytoma cells as glioblastomatic cells. In this case, the peptide toxins were extracted from the saliva of the genus *Elaphe*. A combination of the peptide toxins of the genus *Elaphe* with the peptide toxins from the *Loxosceles*, on the other hand, was unsuccessful. The peptide toxins of the genus *Elaphe*, extracted from the saliva of one of the members of the genus *Elaphe*, destroyed the peptide particles from the active substance of the *Loxoceles* venom, so an effect was no longer observable. But the combination of the peptide toxins from *Sicarius* and *Elaphe* spp. had an effect and could pass, with the help of the peptide toxins from *Latrodectus*, through the blood-brain barrier.

The extraction of peptide toxins can be achieved by known methods. Reference is made to the disclosure of PCT/EP00/12902. Through various chromatographic procedures, for example HPLC techniques, certain mixtures of poisons can be completely divided into individual fractions and then the fractions can be studied in terms of their effects. The destructive effects on tumor cells of certain fractions of the peptide toxins can be defined in experiments performed with the help of cell culture. The efficacy of the tumor-cell-destroying toxin peptide fractions in connection with the blood-brain barrier penetrating substance from *Latrodectus* can then be determined in known animal models. Examples in this regard are found in PCT/EP00/12902, the contents of which are incorporated herein in its entirety. As described in PCT/EP00/12902, through the peptide toxins from *Sicarius*, the expert can isolate the particles with effect from the peptide toxins of the *Elaphe* saliva and the total venom cocktail of the spiders of the genus *Latrodectus* and test them in the way presented above. Here reference is made to PCT/EP2006/063281, the contents of which are incorporated herein in its entirety. This application shows the use of the peptide toxins from *Latrodectus* which can pass through the blood-brain barrier and simultaneously shows the ability to let also other peptide toxins pass through the blood-brain barrier, namely those of *Sicarius* and *Elaphe*.

Alternatively, the whole venom of a spider of the genus *Latrodectus* can be employed rather than the fractions of peptide toxins. In all cases it is very important that the Latrotoxin is largely removed from the venom cocktail, so the pharmaceutical composition, which contains the complete venom or part of the *Latrodectus* venom, can be used as a means of crossing the blood-brain barrier brain without being a danger to patients. Currently, the Latrotoxins alpha and gamma are known. These must be removed at least to such an extent that toxic side effects can be excluded in the case of accumulation in patients. Preferably, only those fractions from the whole venom cocktail of *Latrodectus* in the pharmaceutical composition can be used which contain the active ingredients, which are capable of passing the blood-brain barrier or allow the anti-tumor agents from *Sicarius* and *Elaphe*, to overcome this barrier According to a preferred development of the present invention, the pharmaceutical composition contains additionally inactive parapoxvirus ovis, in particular of strain D1701. Especially preferred are the commercially available preparations with the name ZYLEXIS® from Pfizer. The inactivated parapoxvirus ovis, of D170 strain, to which additionally poligeline and aqua have been added for injection.

1 ml of resuspended ZYLEXIS® contains:

| | |
|---|---|
| Inactivated parapoxvirus ovis, of strain D1701 min. | 230 units of IFN* |
| poligeline | approx. 25 mg |
| aqua for injection | to 1 ml |

*The unit of interferon(s) are determined by an effectiveness test.

According to a preferred embodiment of the present invention, the spiders of the genus *Sicarius* will be selected from the group consisting of the species *Sicarius oweni, Sicarius testaceus, Sicarius hahni, Sicarius albospinosus, Sicarius brasiliensis, Sicarius terrosus*, and *Sicarius terrosus formae*.

The spiders of the *Latrodectus* and *Sicarius* genera are preferably milked in order to recover total venom cocktails.

The spiders are milked mechanically, without the electrical stimulation of the poison glands, at temperatures between 21 and 27° C. The milking process is accomplished in a sterile space, under a stereo magnifying glass; it is observed through the magnifying glass if the spiders bite in the capillaries, as it is important that they do not tear them, because the digestive enzymes can destroy the peptide toxins. The venom cocktails thus obtained are fractionated into component parts through a basic chromatographic process and/or other generally application techniques.

In example 2 the extraction of the peptide toxins from *Sicarius* is described in more detail. The specifics of the peptide toxin extraction from *Sicarius*, which are applicable also to those of *Elaphe* and *Latrodectus*, are described in PCT/EP00/12902, so the expert can easily obtain fractions of the spider venom based on the prior art technique.

According to another preferred embodiment of the present invention, the peptide toxin of the spiders of the genus *Sicarius*, is the peptide toxin HT1 and/or HT2. In example 2 the way of obtaining this peptide toxin is described in detail.

According to another preferred embodiment of the present invention, the composition also contains Lachesis D6. Lachesis D6 of DHU (German Homeopathic Union) is preferred as a solvent for the peptide toxin from *Sicarius*. Lachesis D6 particularly can be preferably used in the production of the composition.

According to another preferred embodiment of the present invention, the spiders of the genus *Latrodectus* are selected from the group consisting of *Latrodectus bishopi, Latrodectus curacaviensis, Latrodectus dahli, Latrodectus erythromelas, Latrodectus hasselti, Latrodectus katipo, Latrodectus menavodi, Latrodectus rhodesiensis, Latrodectus revivensis, Latrodectus schuchi, Latrodectus tredecimguttatus, Latrodectus variolus, Latrodectus hesperus, Latrodectus corallinus, Latrodectus geometricus*, and *Latrodectus obscurior*.

According to another preferred embodiment of the present invention, the species of *Latrodectus* spiders is preferably selected from the species *Latrodectus geometricus* and *Latrodectus obscurior*.

In another embodiment of the present invention, a mixture of the venoms of *Sicarius* or *Latrodectus* can be used. The mixture may be of different types of *Sicarius* or *Latrodectus* species or also the mixture of different populations of a type.

The second aspect of the present invention relates to the use of a pharmaceutical composition, like the one described above, to produce a medicine to treat brain tumor and glioblastoma, particularly to treat an oligodendroglioma.

The inventive combination of venoms or venom fractions of animals of the genus *Sicarius* or saliva of the genus *Elaphe* with a venoms or venom fractions of animals of the genus *Latrodectus* overcome the blood-brain barrier. The venom of *Latrodectus* animals serves as a penetrant which allows penetration of the barrier.

Another aspect of the present invention, refers to a method for preparing a composition comprising the following steps:
Preparing a isotonic solution (0.9%) of sodium chloride *Sicarius* peptide toxin;
optionally adding of a further *Sicarius* peptide toxin to the solution of sodium chloride;
addition a total venom or a venom fraction from the spiders of the genus *Latrodectus*; and
mixing the components, in particular by agitating the mixture.

According to a preferred embodiment of this aspect, an additional immunomodulator, preferably parapoxvirus ovis, more preferably of strain D1701, will be added before mixing.

According to a preferred embodiment of this aspect, at least one peptide toxin of *Sicarius* is dissolved in Lachesis D6 before adding to the solution of NaCl, and preferred both peptide toxins of *Sicarius*.

According to another preferred embodiment of this aspect, the first toxin of *Sicarius* peptide is a peptide toxin *Sicarius*-HT1 and/or the second peptide toxin of *Sicarius* is a peptide toxin *Sicarius*-HT2.

Also preferred as passing substances are the pharmaceutical preparations of phospholipase of the types of *Sicarius* which facilitate the update of the peptide toxin by the tumor cells. The substances of this type and their extraction are described for example in PCT/EP00/12902.

Another aspect of the present invention relates to a kit of parts for treating brain tumors and glioblastoma, comprising a pharmaceutical composition as described above and an incense extract and/or bamboo leaves.

The main components of the incense are the resins in which *boswelia* acids and essential oils are found. In addition to the *boswelia* acids, which belong to the pentacycilic triterpenes group, a tetracyclic triterpene, the acid of tirucal, is also found in the resin.

Preferably, in the present invention the H15 Ayurmedica preparation is used. It relates to tablets which contain a standard level of 400 mg of dry extract of *Boswelia cerata*. The dosage is adjusted depending on the need. It may vary widely, usually between the values of 3 tablets every week up to 25 tablets daily, preferably being 10 tablets weekly up to 20 tablets daily.

The incense extract is used as an alternative to cortisone in order to prevent brain edema in the case of treatment with the appropriate pharmaceutical composition of the present invention. Edema appears in a large number in the case of treatment of brain tumors, especially when they are destroyed very quickly, i.e., where they diminish very quickly.

In the followings the various poisonous substances are explained in detail.

The tumor cells are destroyed by using the peptide toxins which are extracted from the poison of the animals in the genus *Sicarius*, spiders with six eyes. The species *Sicarius oweni, Sicarius testaceus, Sicarius hahni, Sicarius albospinosus, Sicarius argentinensis, Sicarius brasiliensis, Sicarius terrosus* and *Sicarius terrosus formae* are preferred for extracting the poison.

The most preferred peptide toxin is the extracted from the species *Sicarius oweni, Sicarius testaceus, Sicarius argentinensis, Sicarius terrosus* and *Sicarius terrosus formae*, with the last two species being the most preferred.

The peptide toxins can be extracted by generally known separation techniques, such as for example by gel electrophoresis or chromatography, especially column chromatography. The extraction of the primary poison cocktail from spiders is described below.

Alternatively or additionally the saliva of the vipers from the genus *Elaphe* can be used. The saliva are extracted by placing a cotton swab in front of the snake, which eventually the snake may bite. The saliva present on the cotton swab can be extracted from the swab with the help of a dissolution means, such as Lachesis D6 or a solution of 0.9% NaCl. The resulting solution can be concentrated by known procedures.

For passage through the blood-brain barrier, the active substances from the venoms of the spiders of the *Latrodectus* species ("black widow") are preferred. These belong to the Family of spheric spiders (*Theridiiade*). The characteristic of these animals is a large posterior region, reminiscent of a sphere. The anterior region of the body is very small in comparison. Males reach a length of 5 mm without legs, and the females mostly between 10 and 18 mm. These animals have a brownish color to shiny black. Almost always, marks of red, orange, or yellow are found on the posterior of the body. They can be found in the different, and are sometimes are also found in cities. The forest is not generally accepted as a habitat.

Preferably, the following species can be employed:
a) *Latrodectus bishopi*
b) *Latrodectus curacaviensis*
c) *Latrodectus dahli*
d) *Latrodectus erythomelas*
e) *Latrodectus hasselti*
f) *Latrodectus katipo*
g) *Latrodectus menavodi*
h) *Latrodectus rhodesiensis*
i) *Latrodectus revivensis*
j) *Latrodectus schuchi*
k) *Latrodectus tredecimguttatus*
l) *Latrodectus variolus*
m) *Latrodectus hesperus*
n) *Latrodectus corallinus*

The last two species are particularly preferred for passage through the blood-brain barrier, especially in cases where the patients who are treated are children.

For the composition according to the present invention, the species *Latrodectus geometricus* and *Latrodectus obscurior* are particularly preferred.

The Black Widow, as it is known in homeopathy, is found mainly in America, along the Pacific Coast, to Canada. The homeopathically-prepared venom from the black widow is an important substance for the treatment of Angina pectoris. This spider usually stays away from popular localities and lives near the ground, among stones and brushwood. However, where a spider is found, there usually are several in the immediate vicinity.

*Latrodectus bishopi* occurs in central and southern Florida.

*Latrodectus curacaviensis* occurs in the areas of North America and South America, and in the Netherlands Antilles. The females are of shiny black color on the whole body, and on the abdomen have striking marks of red or orange color. The legendary poison is quite dangerous to people, but in rare cases it can also be lethal.

*Latrodectus dahli* is found in Iran.

*Latrodectus erythromelas* occurs in Sri Lanka.

*Latrodectus hasselti* is encountered from India to New Zealand and is often found in basements, garages, barns and exterior toilets. These spiders also can be found under batches of wood or under other construction materials or debris.

*Latrodectus katipo* is the only poisonous spider in New Zealand. It is found mostly in the artificial environs of New Zealand, except for the extreme South. It is found near the soil, in the grass or cut wood. The bite of the Katipo spider can be deadly, especially as the antidote has its effect in three days.

*Latrodectus menavodi* is found in Madagascar and the Seychelles.

*Latrodectus rhodesiensis* lives in southern Africa.

*Latrodectus revivensis* lives in Israel, especially in the Negev.

*Latrodectus schuchi* (now known as *Latrodectus lilianae*) is found in Europe only in Spain, specifically in Aragon.

*Latrodectus tredezimguttatus* is found in southern Europe, frequently on fields of grain, especially in the Mediterranean, but also in Asia and Africa. The appearance of these spiders is characterized by a body entirely of glossy black, with 13 red spots on the back side. The often irregular net that is woven is often found nearby the soil. Because new weaves and new threads are always woven into this net, it is very stable. The center of the net forms a basket shaped net and often is found under an object, such as a rock, a branch or even the crack of a wall.

*Latrodectus variolus* is found for example in America in Michigan. Female specimens have a red dot on the inferior part of their posterior. Males do not have this feature, but they have a red and yellow stripe on the back.

The venom of *Latrodectus* is composed of 6 to 7 proteins, with molecular weights from 5 kDa up to 130 kDa, of which Latrotoxin is a highly effective neurotoxin. The complete poison cocktail or part of the poison of the *Latrodectus* species referred to in paragraphs a) to n) is used, and in particular of the species *Latrodectus geometricus* and *Latrodectus obscurior*. The *Latrodectus* species referred to in paragraphs m) and n) can be used also for children under the age of about 12 years old.

The substances used according to the invention for the pharmaceutical composition may be obtained naturally from animals. These poisons were originally developed to capture prey and to predigest animal protein. This natural mode of action may be obtained by a function-preserving, careful extraction of the venom components (e.g., by manual milking).

In contrast to the traditional methods of milking from anthropods using an electrical method (see Weickmann D. (1991): The attitude and the poison of the Sicariidaes. Arachronologic Index 16, p. 12-13; Weickamnn D., Burda R (1994): Electrophoresis of scorpion venoms. Electrophoresis Forum 1994, Abstracts, Technical University of Munich), in which the poison is obtained from animals with an electrical impulse that causes the contraction of the venom glands of the animals (animals are here preferably cooled), according to the present invention the cocktail of venom is obtained through a manual method by which the animals are stimulated using their natural behavior of defense to release the poison.

According to one embodiment of the invention, a way of manually milking the spiders is provided. This way genuine, unadulterated venom will be obtained, while in contrast, for example in the electrical milking by electron flow restructured substances or molecules are obtained which can be changed in their modes of action, or substances in the toxins can be present that the animal would not otherwise make. These substances may, but need not necessarily affect the efficiency of the poison cocktail, rendering the medically-active compound inactive. By default, an analysis and/or quality control performed using standard electrophoretic methods.

For manual milking, subadult females from the genera and species mentioned above can preferably be used, these being fixed with a finger of a hand in a position on the back, and are stimulated to release the venom by tapping with a part of the trunk of a sterile cannula positioned on a sterile syringe at the maxillaries. The room temperature is usually between 21 and 27 degrees, air moisture of 50% up to 70%. The day time does not matter.

It is preferred that the stimulation time must not last more than 90 seconds, otherwise the animal will be exposed to unnecessary stress. After the appearance of the poison drop on the poison fangs, the venom is brought into the syringe through the cannula. Subsequently, the cannula will be closed with a cannula protector. The closed syringe, together with the collected venom, will at the end be brought directly into a desiccator.

It is also possible that the active substances described herein, which are found in various animal venoms, can be chemically synthesized or produced by molecular biological methods in recombinant form. As is usual in the case of chemical substances, the present invention includes also derivatives and salts of the inventive substances. For example, the peptide toxin may contain one or more substitutions and/or deletions of amino acids, wherein the inventive medical effect has been maintained. The extraction of the described active substances takes place by the traditional methods of chemical process engineering.

The active substances of the present invention are preferably used in the form of a pharmaceutical composition in which they are mixed with carriers or carrier materials in doses, so that the disease is treated or at least mitigated. Such a composition can contain (in addition to the active materials and the carriers), diluents, fillers, salts, buffers, stabilizers, solubilizers and other materials which are well known in the art. The term "pharmaceutically acceptable" is defined as a non-toxic material that does not interfere with the effectiveness of the biological activity of the active ingredient or active ingredient. The selection of the carrier depends on the route of administration.

The pharmaceutical composition may further comprise other materials that increase the activity of the active substance or complement its activity or its use in the treatment. Such complementary factors and/or means may be contained in the pharmaceutical composition, which can achieve a synergistic effect and can minimize side effects or undesirable effects.

The formulation techniques, respectively for preparation and administration of the compounds of the present registration, can be found in *Remington's Pharmaceutical Sciences*, Mack Publishing Co., Easton, Pa., latest edition. An effective dose from a pharmaceutical point of view relates to an amount of a compound that is enough to achieve an improvement in symptoms, for example the treatment, cure, prevention, or improvement of certain conditions. The appropriate modalities of administration may include for example oral administration, rectal and transmucosal or intestinal and parental administration, including also the administration by intramuscular injections, subcutaneous, intramedullary, as well as intrathecal, direct intraventricular, intravenous, intraperitoneal or intranasal injection. Subcutaneous or intramuscular administration will be considered to be preferable for patients.

Administrated will be 1-5 ml, preferably 2-4 ml of composition every 1-4 days. The amount of a composition administered may be adjusted by a specialist. This match may be modified during the treatment.

In the case of the traditional treatment methods, both in the case of primary tumors as well as in the case of the secondary or of relapse tumors, edema can be formed, causing severe pain upon pressure. Cortisone is used to prevent formation of edema, often even in very high doses. Cortisone, however, can still cause tumors. Also, cortisone can create a strong dependence, so that the withdrawal will be gradual, slow, with partial reduced doses.

The inventors of the present invention have ascertained that the compositions corresponding to the invention are disturbed at their passage into the brain by the cortisone. The inventors surprisingly found that the extract of incense and/or bamboo can be used as an absolute substitute against the formation of the edema.

As mentioned above, especially the preparations of H15 as incense extracts are taken into consideration. And the extract of bamboo is in particular the extract from the leaves of bamboo. Directly dry leafs of incense and/or bamboo leaves in the form of capsules can be used in combination with the pharmaceutical composition that can be administered according to the present invention.

In the following the production and the effect of the inventive pharmaceutical composition will be presented through examples. These examples are only exemplary and will not in any way limit the invention.

For the production of a pharmaceutical composition in the form of an injectable solution, 1 ml of saturated solution of peptide toxin HT1 of *Sicarius* in Lachesis D6 DHU (German Homeopathic Union) is introduced into 30 ml a solution of 0.9% NaCl. Finally, 1 ml of saturated solution of the peptide toxin HT2 of *Sicarius* in Lachesis D6 DHU is added. It is preferred that both phases are carried out at room temperature.

This cocktail mixture is completed by addition of a substance of *Latrodectus geometricus* and/or *Latrodectus obscurior*. In addition to this the venom of different populations of *Latrodectus geometricus* and/or *Latrodectus obscurior* can be used.

1 ml of ZYLEXIS® from the company Pfizer can be added as immunomodulator.

Finally, the resulting mixture can be mixed 10 times towards the center of the earth.

The resulting composition can be stored at approximately 7° C., in darkness, for 9 months. The loss of effect, established experimentally (electrophoretically) after a period of 9 months is 10%.

COMPARATIVE EXAMPLE 1

In a cell culture flask (1250 ml) the effect of the different extracts of venom were defined through the number of cells after 24, 48 and 100 hours, as it appears in Table 1 below. Here it is seen that the population of cells decreases in an insignificant number. The decrease of the population of cells in vitro corresponds to the decrease of a tumor in vivo.

| Substance for passing through the blood-brain barrier, means of dissolution described in DE 10 2005 027 665 | Substance that destroys the brain tumor, always with *Androctonus bicolor* | Substance result from combination of venom of the spiders, by counting the cells at: 24 | 48 | 100 h |
|---|---|---|---|---|
| *Latrodectus bishopi* | *Sicarius* sp./ *Varanus* sp. | ca. 80% | 85% | 94% |
| *Latrodectus curacaviensis* | *Sicarius* sp./ *Varanus* sp. | ca. 50% | 70% | 80% |
| *Latrodectus dahli* | *Sicarius* sp./ *Varanus* sp. | ca. 40% | 42% | 43% |
| *Latrodectus erythromelas* | *Sicarius* sp./ *Varanus* sp. | ca. 52% | 64% | 93% |
| *Latrodectus hasselti* | *Sicarius* sp./ *Varanus* sp. | ca. 49% | 72% | 85% |
| *Latrodectus katipo* | — | | | |
| *Latrodectus menavodi* | — | | | |
| *Latrodectus rhodesiensis* | — | | | |
| *Latrodectus revivensis* | *Sicarius* sp./ *Varanus* sp. | ca. 70% | 71% | 70% |
| *Latrodectus schuchi* | *Sicarius* sp./ *Varanus* sp. | ca. 80% | 90% | 94% |
| *Latrodectus* | *Sicarius* sp./ *Varanus* sp. | ca. 95% | 95% | 9% |
| *tredecimguttatus* | *Sicarius* sp./ *Varanus* sp. | ca. 83% | 88% | 91% |
| *Latrodectus variolus* | *Sicarius* sp./ *Varanus* sp. | ca. 24% | 20% | 20% |
| *Latrodectus hesperus* | *Sicarius* sp./ *Varanus* sp. | ca. 31% | 17% | 11% |
| *Latrodectus corallinus* | | | | |

Example 1

Similarly to Comparative Example 1 above, the compositions of the present invention have been searched, as follows in Table 2:

| Substance that destroys the tumor cells, without *andoctonus bicolor* | Substance for passing through the blood-brain barrier | Number of cells by: 24 | 48 | 100 h |
|---|---|---|---|---|
| *Sicarius oweni* | *Latrodectus geometricus* | 40 | 40 | 27% |
| *Sicarius testaceus* | RSA | 39 | 30 | 12% |
| *Sicarius hahni* | | 34 | 31 | 30% |
| *Sicarius albospinosus* | | 51 | 50 | 53% |
| *Sicarius argentinensis* | | 49 | 44 | 46% |
| *Sicarius brasiliensis* | | 42 | 40 | 28% |
| *Sicarius terrosus* | | 51 | 23 | 8% |
| *Sicarius terrosus* formae | | 58 | 18 | 3% |
| *Sicarius oweni* | *Latrodectus obscurior* | 45 | 40 | 29% |
| *Sicarius testaceus* | Madagascar | 51 | 50 | 45% |
| *Sicarius argentinensis* | | 38 | 40 | 39% |
| *Sicarius terrosus* | | 62 | 51 | 48% |
| *Sicarius terrosus* formae | | 53 | 50 | 11% |
| *Sicarius oweni* | *Latrodectus geometricus* | 41 | 32 | 30% |
| *Sicarius testaceus* | America de Sud | 37 | 37 | 38% |
| *Sicarius argentinensis* | | 44 | 40 | 31% |
| *Sicarius terrosus* | | 49 | 40 | 18% |
| *Sicarius terrosus* formae | | 59 | 32 | 9% |

It is shown here that after increased incubation of the cells the growth of the cells does not take place anymore. Usually the toxin from the *Sicarius* kills the tumor cells in an increased way. Phospholipase from *Sicarius argentinensis* is used as a passing enzyme. This crossing substance is available in sufficient quantity, and it enables the diffusion of the peptide toxins, as for example of *Sicarius* toxins, in the tissues and in the cells.

Example of Therapy

For the therapy of the brain tumors a subcutaneous injection of 2-4 ml of the composition according to the invention are administrated to the patient every two or three days, according to the severity of the patient's disease. The course of therapy is monitored by positron emission tomography (PET) and the tumor marker LSA (sialinic acids with lipids). Accordingly, the therapy can be adjusted if necessary.

In addition up to 20 tablets of H15 or 3 capsules of incense leaves are administrated daily in order to prevent the formation of an edema, which can also result in faster tumor destruction.

The capsules containing extracts of incense leaves also comprise dry extracts of *Bamboo ventricosa.*

Conduct of the treatment through various examples of patients:

patient, born in 1999, glioblastoma diagnosed in $1^{st}$ year of life. Inoperable, only 6 irradiations received until July 2000. In June 2001 started the therapy with the composition corresponding to the present invention, 3 ml daily for 5 days, then until September 2005 2.5 ml each 2nd day, from October 2005 every 3 days. From February 2002 the girl goes again to kindergarten and feels good. LSA "started" at 27 and from November 2001 oscillated at 23. 1 time per week the child received 2 capsules of incense in order to prevent the formation of a strong edema. PET was not significant since 2003. The last severe headaches were observed in December 2002.

patient, born in 1958, astrocytoma of grade II, diagnosed in May 2000. Was presented to a doctor in Munich in June 2000 after the first operation. Received 15 irradiations after the surgery and began the Caelix chemotherapy, which he has tolerated poorly. In the computerized tomography, a strong diffuse enlargement of the tumor was presented until September 2000, and depending on the type of cells also a glioblastoma. In October 2000 the patient wanted to begin the therapy with the spider venom. He started with a dose of 4 ml daily, between 3-7 Oct. 2000. Then later until the 2 Jan. 2002 received 3 times daily injections. From January 4 and until December 2006, 2.5 every 2 days. The overall results of the patient were good, in September 2006 a very poorly active outbreak of tumors was still approximately 0.7 cm high in PET, on the right side. The LSA after the surgery was 31, by the end of November 2000 at about 25, and then from 2004 leveled off at approximately 20.5. The patient was administrated 12 tablets of H15 since 14 Jan. 2001 on a daily basis.

patient, born in 1943, diagnosed in October 2002 with glioblastoma. The patient refused surgery because he no longer hopes for improvement. Takes even today daily 10 tablets of H15 and 1.5 ml of the inventive composition every 2nd day. PET was since the admission into hospital from October 2004 insignificant! LSA started in 2003 from 26,2, and now is at around 19.

patient, male, at the age of 3 years experienced reduced vision. At 6 years was diagnosed with brain tumor on the optic chiasm. Subsequent radiotherapy did not proceed positively. After an increase in intracranial pressure several probes, so-called shunts, were placed in order to reduce intracranial pressure. At the age of 9 years the patient had a life time predicted to be a few weeks. The therapy using the pharmaceutical composition according to the present invention began with a dose of 2 ml of the composition administered intramuscularly. After an initial interval of 6 days, with an interval of 2 days, 1 ml of the composition was administered intramuscularly. In the course of 2 weeks, the dose rose slowly to 2 ml. One month after initiation of therapy, a computer tomographic image showed slight shrinkage of the tumor. After about a year, a significant shrinkage of the tumor was visible. The dosage was then increased from 2 to 3 ml, and the administration was prolonged from 2 days to 3 days. At 13 years, the patient was in a state that has allowed him to participate in regular life.

Example 2

General Representation of a Procedure of Basic Chromatographic Separation

To separate the fractions of effective peptide toxins from the total venom cocktail from the spiders of genus *Latrodectus* and *Sicarius*, as well as from the vipers of the genus *Elaphe*, procedures of basic chromatographic separation are preferred. Of course, the specialist may also apply other procedures for separating the mixture of peptides. The individual fractions, resulting from the separation process, are verified in terms of their capacity, or by cell culture or by animal experiments. The use of the individual fractions of the *Latrodectus* total cocktail as a crossing agent through the blood-brain barrier comes mainly from probing animal models.

General representation of a procedure for basic chromatographic separation

For the separation in individual particles/fractions, the total venom will be added to 5 ml of protein solvent solution, for column chromatography, which is composed of 0.25 M Tris/HCL, pH 6.5 up to 7.3, 1.92 M glycine and deionized water. With the total cocktail of venom, a saturated solution will be produced in a TEFLON® vessel. For homogeneous mixing, the total cocktail with the protein solvent solution is shaken for 60 seconds on a Vortex, avoiding the formation of foam.

After homogenization, the solution will be passed through an acrylic glass funnel in a column of transparent acrylic glass, with the interior circumference of 1 cm, the wall thickness of 2 mm and the height of 50 cm, and at the bottom it has a conical shape on the distance of 1.5 mm, but it is open. In the column are 15 mL Gel (ACA 34; Matrix 3%, Acrylamide 4% Agarose; field of fractioning (MW): proteins from 20-350 kDa, exclusion limit 750 kDa, circumference of the balls: 60-140 μm). The introduced venom solution flows through the infiltration in the gel, the solution plugging in the gel. After the total infiltration of the venomous solution in the gel 165 ml of solvent solution (0.25 M Tris/HCl, pH 6.5-7.3, 1.92 M glycine) will be inserted in portions (without allowing the gel to dry) in the column. This solvent solution flows by passage of the venomous solution in the gel. The first 15 mL which will trickle down from the column are the remains of the buffer in the gel and will be discarded. At the end, 40 fractions of 4 mL will be collected.

Through the chemical and physical characteristics of this separation system 4 mL for the individual fractions will result. If in the fractions a single component is found, this fact will be verified through SDS-PAGE. Only one band for each fraction.

For SDS-PAGE, for the protection of the correlations of peptides and proteins, Roti Load 1+2 (Carl Loth GmbH & Co. KG, Karlsruhe: SDS-, Glycerol, bromophenol blue, phosphate buffer, Roti Load 1 with mercaptoethanol, Roti Load 2 without mercaptoethanol) will be used as extraction buffers of the fraction in the gel.

After the separation, the individual fractions will be retained in clean TEFLON® containers that are previously sterilized and can be sealed.

Example 3

Production of the Sicarius Peptide Toxin

Sicarius spiders are milked, as described in detail above, to extract the total venom cocktail. The complete venom is then extracted by a method of chromatographic separation using a column, for example by HPLC. Fractions 4, 8, 11, and 14 contain substances that destroy tumor cells from the species Sicarius oweni, Sicarius testaceus, Sicarius hahni, Sicarius albospinosus. Fractions 5 and 10 contain substances that destroy the tumor cells in the South American species Sicarius argentinensis, Sicarius brasiliensis, Sicarius terrosus and Sicarius terrosus formae.

In the SDS-PAGE electrophoresis results, by the apparent mass of blue color, the following molecular weights (average means) of the frozen-dried substances are obtained:
African Sicarius:

| Fraction 4  | 55 000 | Yes |
| Fraction 8  | 70 000 | Yes |
| Fraction 11 | 82 000 | Yes |
| Fraction 14 | 85 000 | Yes |

South American Sicarius:

| Fraction 5  | 25 000 | Yes |
| Fraction 10 | 81 000 | Yes |

Fraction 4 corresponds to peptide toxin HT1, and fraction 10 corresponds to peptide toxin HT2.

Peptide toxins of Latrodectus and Elaphe were tested as HT1 and HT2 to the venal-glioblastoma standard and cell cultures of astrocytes and also showed the expected effect.

The phospholipase in the total venomous cocktail from Sicarius argentinensis was extracted and defined in the same way as the peptide toxins. The molecular weight is 38,000, by which it is distinguished from other substances from Sicarius. The order on the type of phospholipase could be demonstrated by enzyme kinetic checks.

The invention claimed is:

1. A pharmaceutical composition for treating a brain tumor, comprising a pharmaceutically effective amount of:
   a.) a peptide toxin from a spider of the genus Sicarius, saliva of a viper of the genus Elaphe, or a combination thereof; and
   b.) a fraction of a poison from a spider of the genus Latrodectus, wherein the fraction is devoid of latrotoxin content.

2. The pharmaceutical composition of claim 1, further comprising inactive Parapoxvirus ovis.

3. The pharmaceutical composition of claim 2, wherein the Parapoxvirus ovis is Parapoxvirus ovis group D1701.

4. The pharmaceutical composition of claim 1, wherein the spider of the genus Sicarius is selected from the group consisting of Sicarius oweni, Sicarius testaceus, Sicarius hahni, Sicarius albospinosus, Sicarius argentinensis, Sicarius brasiliensis, Sicarius terrosus, and Sicarius terrosus formae.

5. The pharmaceutical composition of claim 4, wherein the spider of the genus Sicarius is selected from the group Sicarius terrosus and Sicarius terrosus formae.

6. The pharmaceutical preparation of claim 1, wherein the peptide toxin is peptide toxin HT1, peptide toxin HT2, or a combination thereof.

7. The pharmaceutical composition of claim 1, wherein the pharmaceutical composition further comprises Lachesis D6.

8. The pharmaceutical composition of claim 1, wherein the spider of the genus Latrodectus is selected from the group consisting of Latrodectus bishopi, Latrodectus curacaviensis, Latrodectus dahli, Latrodectus erythromelas, Latrodectus hasselti, Latrodectus katipo, Latrodectus menavodi, Latrodectus rhodesiensis, Latrodectus revivensis, Latrodectus schuchi, Latrodectus tredecimguttatus, Latrodectus variolus, Latrodectus hesperus, Latrodectus corallinus, Latrodectus geometricus and Latrodectus obscurior.

9. The pharmaceutical composition of claim 8, wherein the spider of the genus Latrodectus is selected from the group consisting of Latrodectus geometricus and Latrodectus obscurior.

10. The pharmaceutical composition of claim 9, wherein the pharmaceutical composition further comprises a Sicarius phospholipase.

11. A method for treating a patient with a brain tumor or a glioblastoma, the method comprising administering to the patient a therapeutically effective amount of the pharmaceutical composition of claim 1.

12. A method for preparing the pharmaceutical composition of claim 1, the method comprising:
    preparing a solution comprising sodium chloride and a peptide toxin from a spider of the genus Sicarius, saliva of a viper of the genus Elaphe, or a combination thereof;
    adding a fraction of a poison from a spider of the genus Latrodectus, wherein the fraction is devoid of latrotoxin content; and
    mixing the solution and the fraction, whereby a pharmaceutical composition of claim 1 is prepared.

13. The method of claim 12, wherein the pharmaceutical composition further comprises an immunomodulator.

14. The method of claim 13, wherein the immunomodulator comprises an inactive form of Parapoxvirus ovis.

15. The method of claim 12, wherein the pharmaceutical composition further comprises Lachesis D6.

16. The method of claim 12, wherein the peptide toxin is peptide toxin HT1, peptide toxin HT2, or a combination thereof.

17. A kit of parts for treating a brain tumor, glioblastoma, or both, the kit comprising:
    i) the pharmaceutical composition of claim 1; and
    ii) an extract of incense, an extract of bamboo, or a combination thereof.

* * * * *